US008297129B2

(12) United States Patent
Muskopf

(10) Patent No.: US 8,297,129 B2
(45) Date of Patent: Oct. 30, 2012

(54) INSTRUMENT MOUNTING SYSTEM AND METHOD

(76) Inventor: Brian A. Muskopf, Austin, TX (US)

( * ) Notice: Subject to any disclaimer, the term of this patent is extended or adjusted under 35 U.S.C. 154(b) by 128 days.

(21) Appl. No.: 12/817,283

(22) Filed: Jun. 17, 2010

(65) Prior Publication Data

US 2010/0319462 A1  Dec. 23, 2010

Related U.S. Application Data

(60) Provisional application No. 61/218,188, filed on Jun. 18, 2009.

(51) Int. Cl.
 *G01B 7/16* (2006.01)
 *G01L 1/00* (2006.01)
 *G01L 1/24* (2006.01)
(52) U.S. Cl. ............... 73/776; 73/766; 73/775; 73/800
(58) Field of Classification Search .............. 73/800, 73/766, 760, 763, 768, 774, 775, 776
See application file for complete search history.

(56) References Cited

U.S. PATENT DOCUMENTS

| 4,088,509 | A | | 5/1978 | Blaze, Jr. |
| 4,830,515 | A | | 5/1989 | Cortes |
| 4,918,305 | A | * | 4/1990 | Wlodarczyk et al. ..... 250/227.14 |
| 4,972,073 | A | * | 11/1990 | Lessing ..................... 250/227.16 |
| 4,984,904 | A | | 1/1991 | Nakano et al. |
| 5,654,034 | A | | 8/1997 | Tulloch et al. |
| 6,050,723 | A | | 4/2000 | Amra |
| 6,400,884 | B1 | * | 6/2002 | Matano et al. ................ 385/137 |
| 6,536,950 | B1 | | 3/2003 | Green et al. |
| 6,788,873 | B2 | * | 9/2004 | Fritz et al. ..................... 385/138 |
| 6,913,453 | B2 | | 7/2005 | Kalantzis |
| 7,379,632 | B1 | * | 5/2008 | Twerdochlib .................. 385/13 |
| 2007/0193362 | A1 | * | 8/2007 | Ferguson ......................... 73/800 |

* cited by examiner

*Primary Examiner* — Lisa Caputo
*Assistant Examiner* — Jonathan Dunlap
(74) *Attorney, Agent, or Firm* — Meyertons Hood Kivlin Kowert & Goetzel, P.C.; Jeffrey C. Hood

(57) ABSTRACT

Provided is a strain gage mount, including an instrument carrier mount configured to secure a strain gage during use, a specimen mount configured to couple to a specimen during use, and a thermal insulating layer configured to be disposed between the instrument carrier mount and the specimen mount during use.

24 Claims, 8 Drawing Sheets

INSTRUMENT MOUNTING SYSTEM AND METHOD

PRIORITY CLAIM

This application claims benefit of priority to U.S. Provisional Patent Application Ser. No. 61/218,188, entitled "Instrument Mounting System and Method", filed Jun. 18, 2009, by Brian A. Muskopf, which is hereby incorporated by reference in its entirety as though fully and completely set forth herein.

BACKGROUND

1. Field of the Invention

The present invention generally relates to a system and method for mounting instruments and more particularly to a mounting apparatus and method for a fiber optic strain gage carrier.

2. Description of Related Art

Over the past decade fiber optics based sensors have become widely and accepted established in various markets. Fiber optic based sensors are used in numerous applications including the measurement of temperature, displacement, and strain. Some fiber optic sensors are used to extend the measurement of strain and temperature to measure other physical characteristics such as acceleration. Fiber optic sensors may offer several benefits over other types of sensors including reduced sensitivity to electromagnetic interference. Fiber optic sensors are also capable of being multiplexed such that several sensors can operate off of a single optical fiber and can be provided in a small form factor, allowing use in tight spaces.

During use various physical phenomena cause changes in the optical characteristics of a fiber optic based sensors and are used to measure temperature, displacement and strain. Fiber optic strain gages, for instance, do not rely on changes in electrical resistance, inductance or capacitance associated with conventional types of strain gages. Instead, fiber optic strain gages use the correlation of strain or temperature to optical properties such as wavelength frequency, optical phase changes, optical transmittance and optical wave interference.

In some strain gage sensors, one or more fiber Bragg gratings act as the active sensing element. A fiber Bragg grating (FBG) is a type of distributed Bragg reflector constructed in a short segment of optical fiber that reflects particular wavelengths of light and transmits all others. Fiber Bragg gratings are implemented in an optical fiber core as specialized changes to the index of refraction. Strain gages using fiber Bragg gratings may be inherently immune to electromagnetic interference from radio waves, static electricity or lightning discharges. Fiber Bragg grating strain sensors can be connected serially thus dramatically reducing electrical connections and associated cost. The only connection required between serial sensors is an optical fiber. Due to the low signal loss in fiber optics, these strain gages can often be located at a significant distance from any optical strain or temperature gage interrogation and recording instrumentation. Fiber optical strain gages often exhibit better accuracy, repeatability and sensitivity than their conventional counterparts. Fiber optical strain gages can also be located in places that would not otherwise accommodate a large number of individual wires needed for conventional strain gages. In addition, the sensing element of fiber Bragg grating based strain sensors does not typically require active electronics during operation. This helps to ensure safe use of these strain gages in environments where accidental sparks may cause fires or lead to catastrophic explosions, such as certain oil and gas and other industrial environments. Oftentimes, these characteristics make fiber optic based sensors a feasible choice for these hazardous environments.

Despite the favorable characteristics of certain types of sensors, such as fiber Bragg grating based strain sensors, certain limitations may exists. For example, current fiber Bragg grating-based strain sensors often have operating temperature limitations that may limit their potential uses. For example, certain sensors may not be used where the temperature at or near a surface of a test object is outside of the accepted operating temperature range.

Accordingly, there is a desire for a system and method for using fiber optic sensors that enables them to be used in environments that may otherwise be outside of their operational limits, such as a high temperature environment, while maintaining operational characteristics, such as measurement accuracy.

SUMMARY

Various embodiments of instrument mounting systems and related apparatus, and methods of operating the same are described. In one embodiment, a method includes a strain gage mounting system. The system includes a thermal shield having a first thermal shield with a first surface configured to face away from a test specimen during use and a second surface configured to face the test specimen during use, a second thermal shield having a first surface configured to face away from a test specimen during use and a second surface configured to face the test specimen during use. The first thermal shield and the second thermal shield are not rigidly coupled to one another. The system also includes a strain gage carrier mount disposed on a first side of the thermal shield such that the thermal shield is disposed between the strain gage carrier mount and the test specimen during use. The strain gage carrier mount includes a first carrier mount rigidly coupled to the first side of the first thermal shield and configured to couple to a first portion of a strain gage carrier and a second carrier mount rigidly coupled to the first side of the second thermal shield and configured to couple to a second portion of a strain gage carrier. The first carrier mount and the second carrier mount are not rigidly coupled to one another. The system also includes a specimen mount disposed on a second side of the thermal shield opposite from the first side of the thermal shield such that the specimen mount is disposed between the thermal shield and the test specimen during use. The specimen mount includes a first specimen mount rigidly coupled to the second side of the first thermal shield and configured to be coupled to a surface of a test specimen, and a second specimen mount rigidly coupled to the second side of the second thermal shield and configured to be coupled to a surface of the test specimen. The first specimen mount and the second specimen mount are not rigidly coupled to one another.

In another embodiment, provided is a strain gage system. The strain gage system includes mounting portion, having a strain gage carrier mount configured to couple to a first end of a strain gage carrier, a specimen mount configured to couple to a surface of a test specimen, and a thermal shield configured to be disposed between the surface of the test specimen and the first strain gage carrier mount.

In another embodiment, provided is strain gage system including a substantially planar thermal shielding plate having a first portion and a second portion that are separate from one another, wherein each of the first portion and the second portion comprise a first surface configured to face a test specimen during use and a second surface opposite the first surface configured to face away from the test specimen during use, wherein the first portion and the second portion are disposed adjacent one another during use, and wherein each of the first portion and the second portion comprise an edge that overlap one another during use. The system also includes a first mount coupled to the first surface of the first portion of the thermal shielding plate via a standoff, wherein an air gap is provided between the first mount and the thermal shielding plate. The system also includes a second mount coupled to the first surface of the second portion of the thermal shielding plate via a standoff, wherein an air gap is provided between the second mount and the thermal shielding plate. The system also includes a first strain gage carrier mount coupled to the second surface of the first portion of the thermal shielding plate via a standoff, wherein an air gap is provided between the first strain gage carrier mount and the thermal shielding plate, and wherein the first strain gage mount is configured to couple to a first portion of a strain gage carrier. The system also includes a second strain gage carrier mount coupled to the second surface of the second portion of the thermal shielding plate via a standoff, wherein an air gap is provided between the second strain gage carrier mount and the thermal shielding plate, and wherein the first strain gage mount is configured to couple to a second portion of a strain gage carrier. The first portion of the thermal shield plate, the first strain gage carrier mount, and the second strain gage carrier mount are configured to move independent of the second portion of the thermal shield plate, the second strain gage carrier mount, and the second strain gage carrier mount.

In yet another embodiment, provided is a strain gage mount, including an instrument carrier mount configured to secure a strain gage during use, a specimen mount configured to couple to a specimen during use, and a thermal insulating layer configured to be disposed between the instrument carrier mount and the specimen mount during use.

BRIEF DESCRIPTION OF THE DRAWINGS

Advantages of the present invention will become apparent to those skilled in the art with the benefit of the following detailed description and upon reference to the accompanying drawings in which.

Figure 1A:
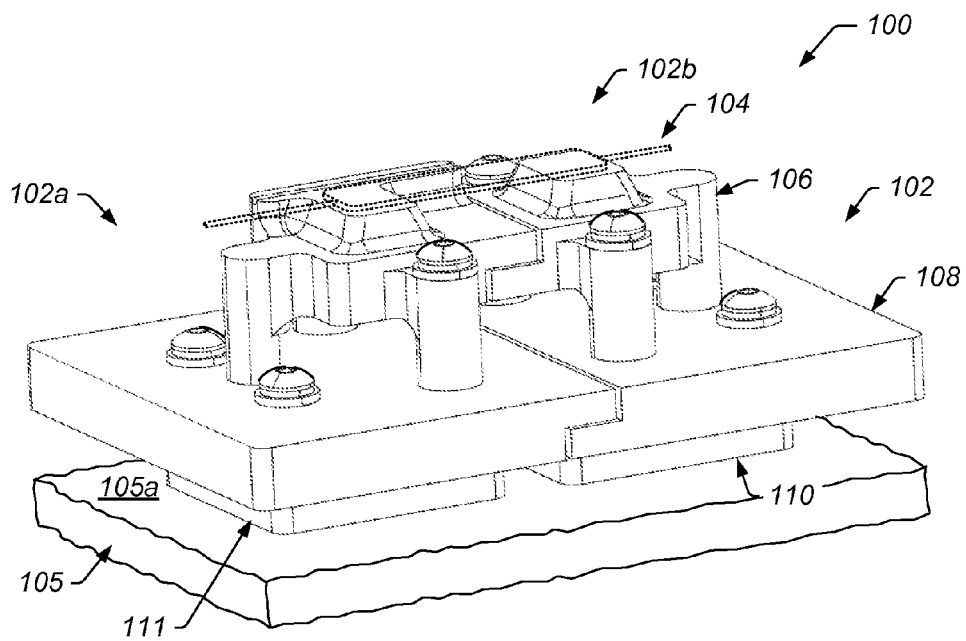
FIGS. 1A and 1B are diagrams that illustrate perspective views of a strain gage system in accordance with one or more embodiments of the present technique.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF ILLUSTRATIVE EMBODIMENTS

As discussed in more detail below, certain embodiments of the present technique include a system and method for using optical sensing devices. More particularly, certain embodiments relate to systems and method for mounting and using a fiber optic strain gage sensor. In some embodiments, a fiber optic strain gage sensor mount includes first and second portions that are mounted to a surface of a test specimen, and include carrier mounts that are couplable to opposite ends of a carrier of a fiber optic strain gage. In certain embodiments, the first and second portions are not rigidly coupled to one another such that they can move relatively freely with respect to one another during use. In some embodiments, the mount includes a thermal shield that is disposed between the test specimen and the carrier mounts and the strain gage during use. The thermal shield may inhibit heat at or near the surface of the test specimen from being transferred to the strain gage. In some embodiments, an air gap is provided between the test specimen and the thermal shield, and/or between the thermal shield and the carrier mounts to further inhibit the transfer of heat to the strain gage. In some embodiments, the air gaps are provided via standoffs located between the respective structures. In certain embodiments, the thermal shield includes a split plate having two portions (e.g., coupled to the first and second portions, respectively, of the stain gage mount) that are not rigidly fixed to one another. In some embodiments, the two portions include an interface (e.g., overlapping edge) that inhibits heat transfer across the thermal shield. In certain embodiments, the carrier mount includes a split plate having two portions (e.g., coupled to the first and second portions, respectively, of the stain gage mount) that are not rigidly fixed to one another. In some embodiments, the two portions include an interface (e.g., overlapping edge) that inhibits heat transfer across the carrier mount. Such embodiments may help to insulate the strain gage from heat. For example, a strain gage coupled to the test object via the mount may be thermally isolated from the test specimen such that heat generated at or near the surface of the test specimen is directed away from the strain gage during use. Accordingly, embodiments of the strain gage system may be used to measure strain of test specimens having a high surface temperature that may otherwise be unsuitable for use with a fiber optic sensor. The gage carrier mount may be quickly and easily attached to a test specimen. Embodiments of the present invention may, thus, provide a high temperature thermally insulating fiber optic strain gage mount that provides the benefits including a pre-mounted strain gage with minimal degradation of strain gage performance while allowing the strain gage to operate continuously at elevated temperatures.

Figure 1B:
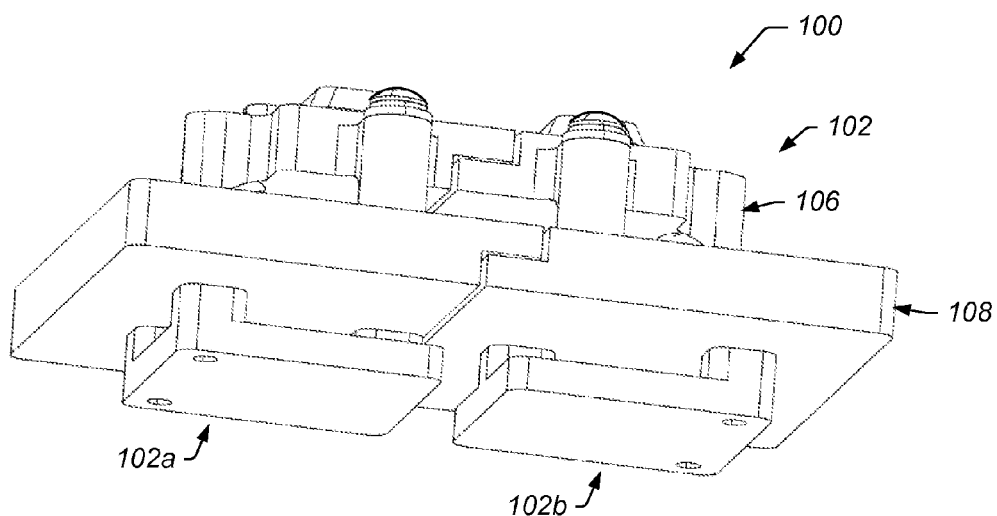
Figure 1C:
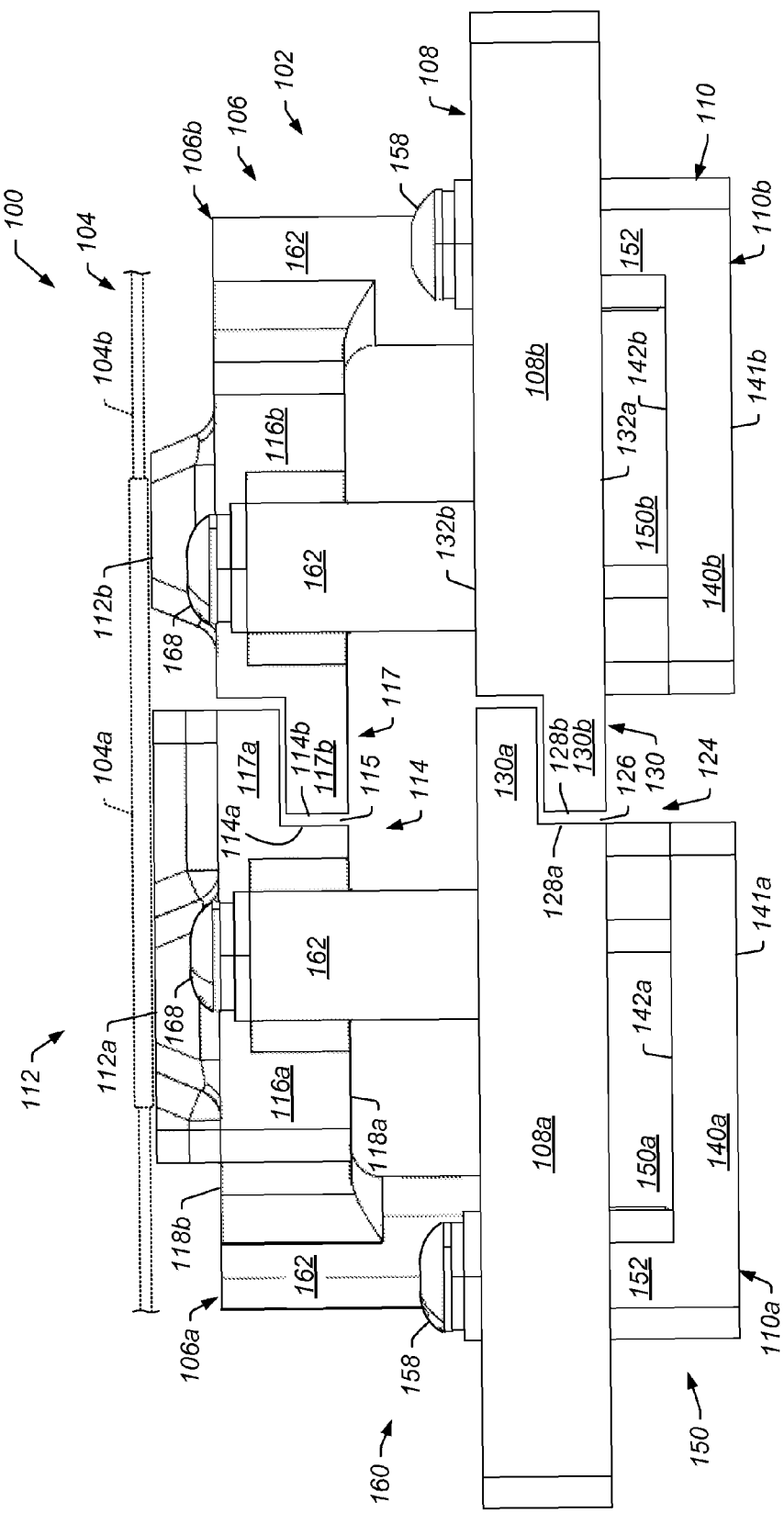
FIG. 1C. is a diagram that illustrates a side view of the strain gage mount system of FIG. 1 in accordance with one or more embodiments of the present technique.
Figure 1D:
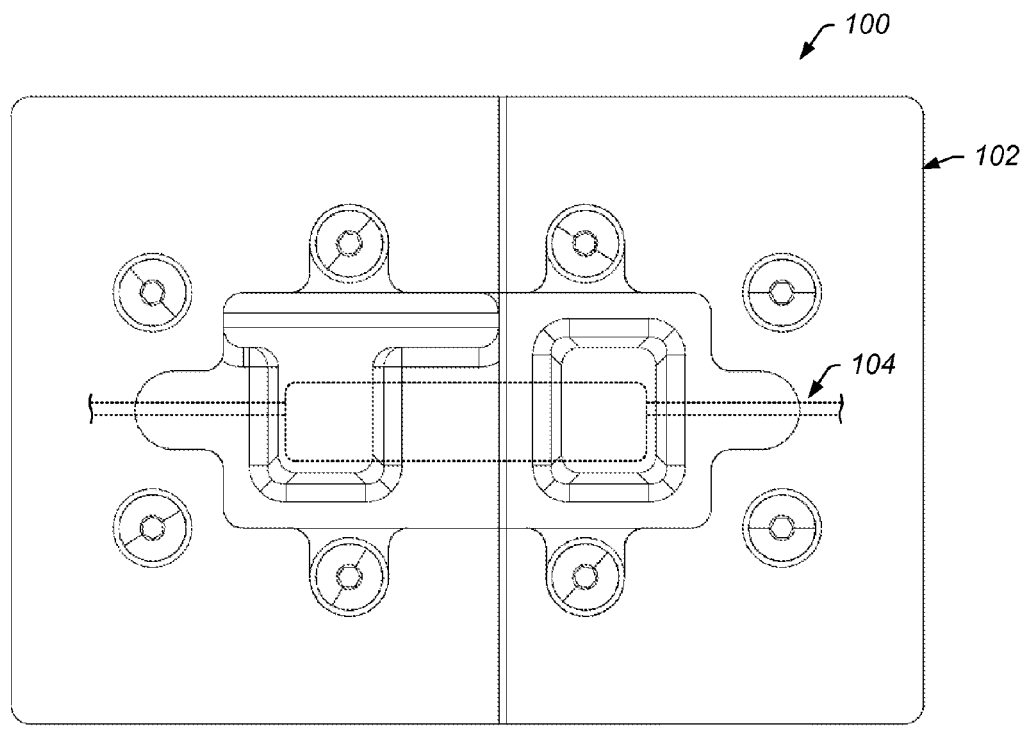
FIG. 1D is a diagram that illustrates a top view of the strain gage mount system of FIG. 1 in accordance with one or more embodiments of the present technique.
Figure 1E:
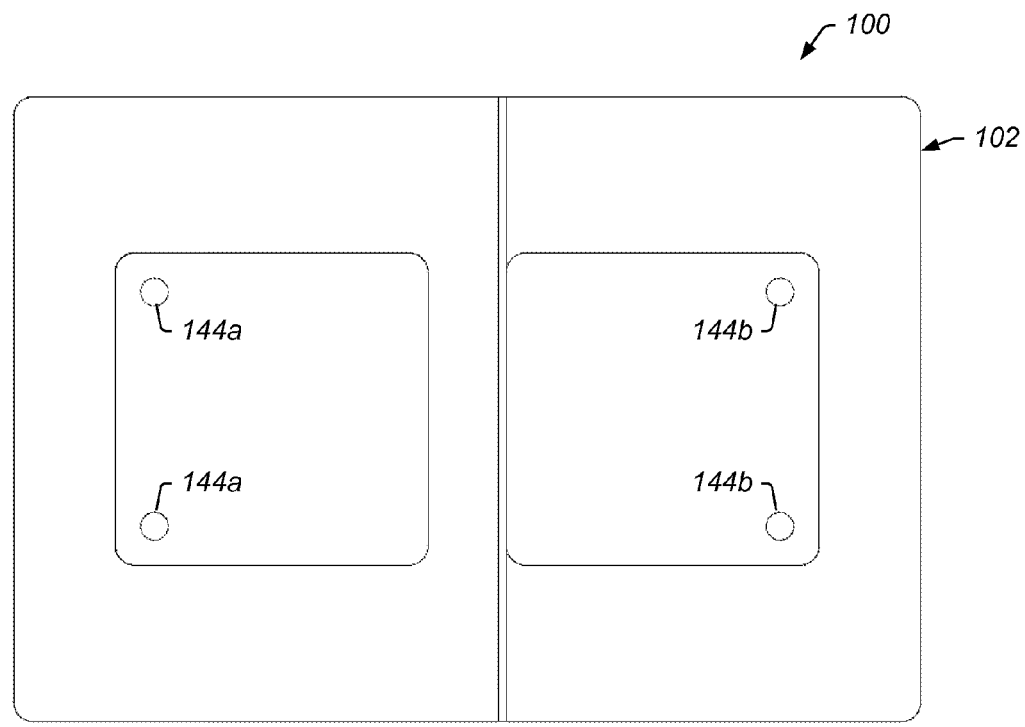
FIG. 1E is a diagram that illustrates a bottom view of the strain gage mount system of FIG. 1 in accordance with one or more embodiments of the present technique.
Figure 1F:
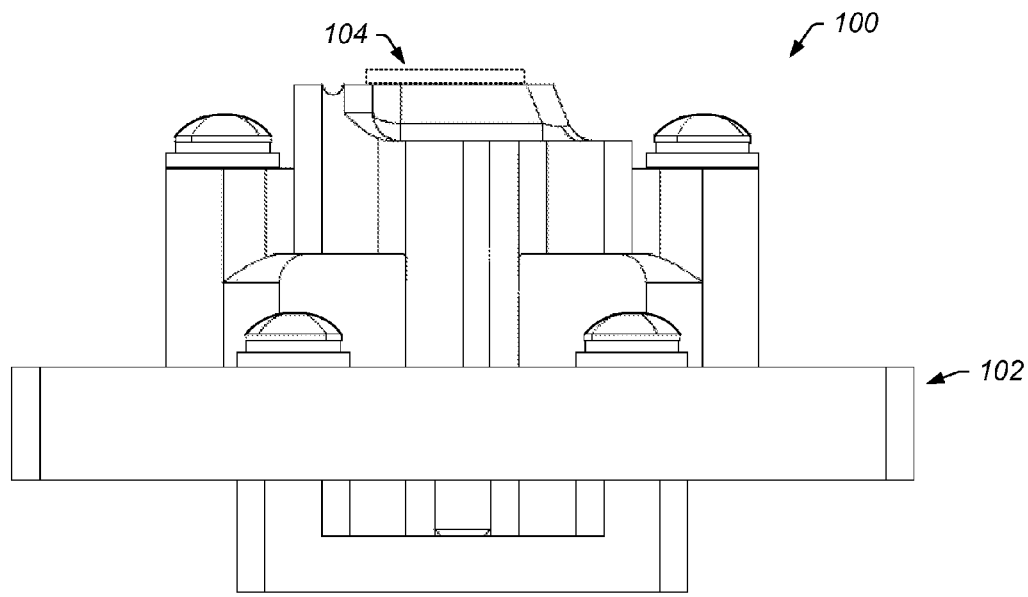
FIG. 1F is a diagram that illustrates an end view of the strain gage mount system of FIG. 1 in accordance with one or more embodiments of the present technique.

Turning now to FIGS. 1A and 1B, depicted are top and bottom perspective views, respectively, of a strain gage system 100 ("system 100") in accordance with one or more embodiments of the present technique. FIG. 1C depict a side view of system 100, FIG. 1D depict a top view of system 100, FIG. 1E depict a bottom view of system 100, and FIG. 1F depict an end view of system 100. In the illustrated embodiment system 100 includes strain gage mount 102 and strain gage 104. Strain gage system 100 may be couplable to a surface 105a of a test specimen 105.

As depicted, in one embodiment, strain gage mount 102 may include two portions disposed proximate one another during use. For example, in the illustrated embodiment, strain gage mount 102 includes a first portion 102a and a second portion 102b. As discussed in more detail below, first portion 102a and second portion 102b may be capable of moving independent of one another such that during use, as a test specimen expands and contracts, first portion 102a mounted on a first surface location of the test specimen is capable of moving independent of second portion 102b mounted on another surface location of the test specimen. Such independent movement may allow first portion 102a and second portion 102b to accurately reflect the relative displacement (e.g., strain) experienced at surface 105a of test specimen 105.

In one embodiment, first portion 102a and second portion 102b may not be directly coupled to one another. For example, in one embodiment, a space, gap, or similar disconnect may exists between all of first portion 102a and second portion 102b such that they are not directly coupled to one another. In such an embodiment, first portion 102a and second portion 102b may be indirectly coupled to one another via surface 105a of test specimen 105 and/or a portion (e.g., the carrier) of strain gage 104. In one embodiment, first portion 102a and second portion 102b may be disposed adjacent one another such that they are in at least partial contact, but remain uncoupled from one another. For example, before during or after installation, first portion 102a and second portion 102b may abut such that at least a portion of their surfaces touch one another even though they are not directly coupled to one another.

In one embodiment, first portion 102a and second portion 102b may be directly coupled to one another. For example, a non-rigid coupling between first portion 102a and second portion 102b may be provided. Non-rigid coupling may enable first portion 102a and second portion 102b to move relative to one another without the coupling significantly impeding their movement. For example, first portion 102a and second portion 102b may be coupled by a pliable/flexible/elastic member or material that couples first portion 102a to first portion 102b but does not provide a sufficient biasing/restoring force that would impede the movement of first portion 102a and second portion 102b such that it would effect a strain reading of strain gage 104 during use. In other words, any affect of coupling between first portion 102a and second portion 102b would be insignificant relative to the desired accuracy of the resulting strain measurement. For example, portions 102a and 102b may be at least partially coupled via a flexible insulating material such as but not limited to polymeric and metalized insulated tape, flexible insulating open and closed cell foams, insulating blankets comprised of stitched and/or woven continuous or discontinuous fibers such as polymers, glass, ceramic, mineral, graphite or carbon, flexible polymers such as polyurethane, nylon, epoxy, etc., and flexible polymer composites such as polyurethane, nylon, epoxy, etc. reinforced with continuous or discontinuous fibers, particles or hollow beads made from metals, polymers, ceramics, glass or minerals, to fill in between or over the gap between the overlap plate edges.

As discussed in more detail below first portion 102a and second portion 102b may be displaced substantially adjacent one another such that gaps between first portion 102a and second portion 102b inhibit/block the movement/transfer of heat from at or near surface 105a of test specimen 105 toward strain gage 104. As discussed in more detail below, certain embodiments may include an overlap, or similar feature that inhibits/blocks the flow of heat from at or near surface 105a toward the strain gage.

As discussed in more detail below, strain gage mount 102 may include one or more portions configured to insulate/isolate strain gage 104 from surface 105a of test specimen 105. For example, as depicted, strain gage mount 104 may provide an offset of strain gage 104 from surface 105a of test specimen 105 during use. As discussed in more detail below, one embodiment also includes a carrier mount and a thermal shield disposed between strain gage 104 and the test specimen during use. The carrier mount and the thermal shield may help to insulate strain gage 102 from elevated temperature by inhibiting the transfer/movement of heat from at or near the test specimen toward to strain gage 102.

In the illustrated embodiment, strain gage mount 102 includes a carrier mount 106, a thermal shield 108, and a test specimen mount 110. Thermal shield 108 is disposed between carrier mount 102 and test specimen mount 110. During use, a bottom surface 111 of test specimen mount 110 may be coupled to surface 105a of a test specimen 105. Carrier mount 106 and thermal shield 108 may be disposed above/offset from surface 105a of test specimen 105. Strain gage 104 may be coupled to carrier mount 106 such that it is disposed above/offset from surface 105a of test specimen 105. The separation/offset between surface 105a of test specimen 105 and strain gage 104 may provide for a lower observed temperature at the location of strain gage 104 relative to the observed temperature at or near surface 105a during use. In some embodiments, additional features, such as portions of carrier mount 106 and thermal shield 108 may help to further reduce the operating temperature at the location of strain gage 104 during use. In one embodiment, strain gage mount 102 provides a pre-tensioning force on fiber optic strain gage 104 allowing measurement of tension as well as compressive strains.

Carrier mount 106 may include a portion of strain gage mount 102 that is capable of securing strain gage 104 during use. For example, carrier mount 106 may fixedly secure at least two portions of strain gage 104 to first portion 102a and second portion 102b of strain gage mount 102, respectively, such that movement relative to one another can be accurately translated to strain gage 104. For example, strain gage mount 106 may provide rigid attachment of fiber optic strain gage carrier 104a to a test specimen at two points while providing little to no resistance to variation in the distance between the attachment points along the longitudinal axis of fiber optic element 104b of strain gage 104.

In one embodiment, carrier mount 106 may include two or more pads 112 (e.g., carrier pads) that are couplable to one or more portions of strain gage 104. For example, in the illustrated embodiment, strain gage mount 102 includes a first pad 112a and a second pad 112b. First pad 112a is provided atop a first portion 106a of carrier mount 106 disposed on an upper portion of first portion 102a that is distal from test specimen 105 during use and second pad 112b is disposed atop a second portion 106b of carrier mount 106 disposed on an upper portion of second portion 102a that is distal from test specimen 105 during use.

Figure 2:
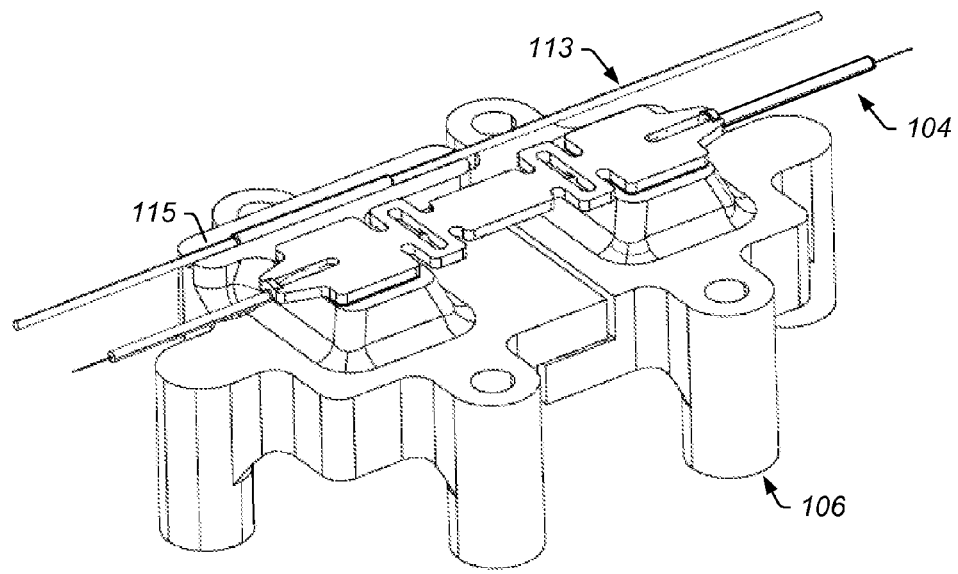
FIG. 2 is a diagram that illustrates a carrier mount and strain gage of the strain gage system in accordance with one or more embodiments of the present technique.

First pad 112a and second pad 112b may fixedly attach to at least a portion of strain gage 102. As depicted in the illustrated embodiment, first pad 112a and second pad 112b may directly couple to carrier 104a of strain gage 104. Strain gage carrier 104a may include a frame that supports a fiber optic strain gage element 104b. In one embodiment, strain gage 104 may include a fiber optic strain gage such as that described in U.S. Patent Publication No. 2007/0193362, the entirety of which is herein incorporated by reference. FIG. 2 illustrates an exemplary embodiment of a strain gage 104 coupled to carrier mount 106 in accordance with one or more embodiments of the present technique. FIG. 2 also illustrates a fiber optic temperature compensation gage 113 bonded to an integral groove 115 of first portion 106a of carrier pad 106.

In one embodiment, first pad 112a and second pad 112b may each attach to portion of strain gage carrier 104a located on opposite sides of an operative portion 104c of fiber optic strain gage 104b. In one embodiment, pads 112 include mechanical fasteners (e.g., screws, bolts, or clips, clamps), complementary protrusions/recesses (e.g., pegs, pins, notches, and holes), an adhesive (e.g., glue), soldering (e.g., metal, alloy or glass soldering), welding (e.g., plastic or metal welding), or the like, or a combination thereof, capable of fixedly securing strain gage 104 to mount 102. In one embodiment, first pad 112a and second pad 112b are spaced at least far enough from one another to accommodate operative portion 104c of fiber optic portion 104b between them. In one embodiment, first pad 112a and second pad 112b are spaced to receive portions of carrier 104a for mounting strain gage 104. For example, first pad 112a and second pad 112b may be located such that they receive complementary mounting portions of carrier 104a.

In one embodiment, carrier pads 112a and 112b may be made of metals or metal alloys, ceramics, glass, minerals, polymer, ceramic, glass or mineral foams, plastics or metal, ceramic, glass, mineral or polymeric matrix composites, or any combination or layering of these materials. In one embodiment, the composite materials are reinforced with but not limited to continuous or discontinuous fibers, particles or hollow beads made from metals, polymers, ceramics, glass or minerals.

In one embodiment, at least a portion of first portion 106a and second portion 106b of carrier mount 106 are disposed proximate one another during use. For example, in the illustrated embodiment, first portion 106a and second portion 106b are separated via a split 114. In the illustrated embodiment, split 114 includes a separation between first portion 106a and second portion 106b. When portions 106a and 106b are separated split 114 provide a gap 115 between the two portions. Gap 115 may be defined by edges of split 114 including a first edge surface 114a of first portion 106a and second edge surface 114b of second portion 106b. Edges 114a and 114b may be disposed close enough to one another to inhibit the transfer of heat from at or near surface 105a of test specimen 105 toward stain gage 104 during use. For example, gap 115 may be about 0.25 mm, 0.5 mm, 1 mm, 2 mm, 3 mm, 4 mm, 5 mm, 6 mm, 7 mm, 8 mm, 9 mm, 10 mm, or more during use.

In one embodiment, carrier mount 106 may include a plate that is disposed under pads 112. For example, in the illustrated embodiment, carrier mount 106 includes a split plate 116 having a first portion 116a and a second portion 116b. In one embodiment, first portion 116a and second portion 116b are not directly coupled to one another. For example, first portion 116a and second portion 116b may include separate plate portions that are disposed proximate one another during use. Split plate 116 may include a plate disposed between thermal shield 108 and pads 112 that helps to inhibit the transfer of heat from at or near surface 105a of test specimen 105 toward strain gage 104 during use. For example, in one embodiment, split plate 116 may include a substantially planar surface having an area larger than that of pads 112a and disposed underneath pads 112 such that it blocks and redirects heat away from and/or around the pads 112, thereby helping to insulate strain gage 104.

In one embodiment, an interface between edges 114a and 114b may be provided to further inhibit the transfer of heat from surface 105a test specimen 105 to stain gage 104 during use. For example, as depicted, one embodiment may include an overlap 117 of at least a portion of first edge surface 114a and second edge surface 114b. In the illustrated embodiment, overlap 117 includes an "S-shaped" overlap. S-shaped overlap 117 includes complementary protrusions 117a and 117b of carrier portions 106a and 106b, respectively, that overlap one another such that gap 115 has a S-shaped path. Overlap 117 and resulting gap 115 may include a path that blocks a straight-line path from a first (bottom) surface 118a of carrier mount 106 facing test specimen 105 during use, to a second (top) surface 118b of carrier mount 106 opposite the bottom surface and facing away from test specimen 105 during use. Protrusions 117a and 117b may be of sufficient length such that as carrier portions 106a and 106b move relative to one another during use, overlap 117 still exists, thereby helping to inhibit the transfer/movement of heat across spilt plate 116 during use.

Figure 3A:
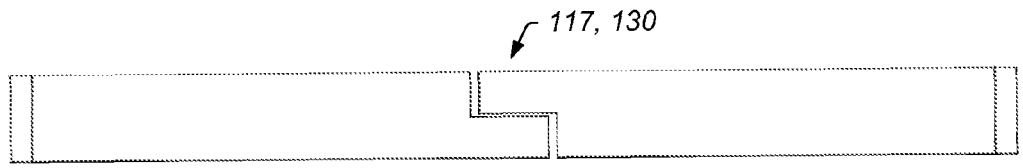
FIGS. 3A-3F are cross-sectional views that illustrate overlapping edges in accordance with one or more embodiments of the present technique.
Figure 3B:
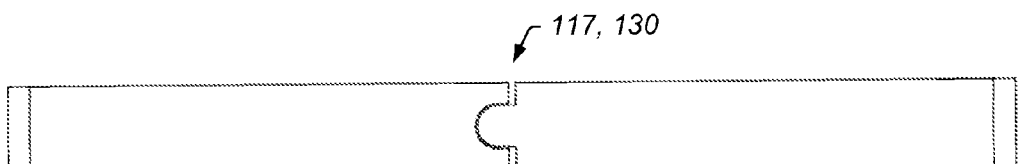
Figure 3C:
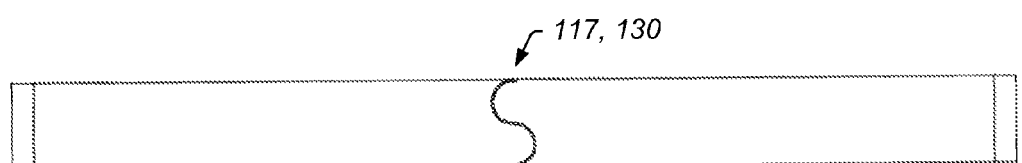
Figure 3D:
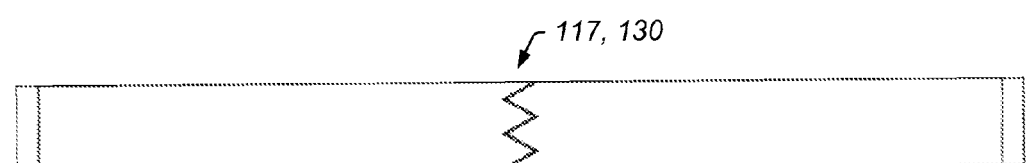
Figure 3E:
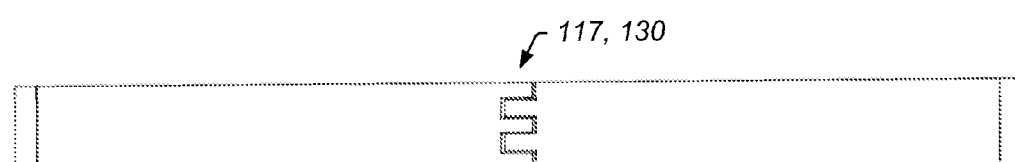
Figure 3F:
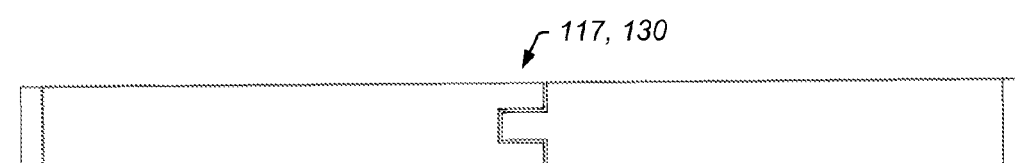

Embodiments may include a various types of fit between first and second portions 116a and 116b of split plate 116. In some embodiments, shapes of the edges 114a and 114b may include variations that provide for a different shape of gap 115. FIGS. 3A-3F illustrates various shapes of overlaps 117 in accordance with one or more embodiments of the present technique. For example, FIG. 3A illustrates an "S-shaped" lipped overlap similar to that described above. FIG. 3B illustrated a single rounded tongue and groove overlap in accordance with one or more embodiments of the present technique. FIG. 3C illustrates rounded lipped overlap in accordance with one or more embodiments of the present technique. FIG. 3D illustrates a saw tooth overlap in accordance with one or more embodiments of the present technique. FIG. 3E illustrates multiple tongues and grooves overlap in accordance with one or more embodiments of the present technique. FIG. 3E illustrates a single tongue and groove overlap in accordance with one or more embodiments of the present technique.

In one embodiment, gap 115 may be spanned by one or more members and materials that provide an elastic, non-rigid, coupling of portions 116a and 116b. For example, gap 115 may employ (e.g., be filled with) a flexible insulating material such as but not limited to polymeric and metalized insulated tape, flexible insulating open and closed cell foams, insulating blankets comprised of stitched and/or woven continuous or discontinuous fibers such as polymers, glass, ceramic, mineral, graphite or carbon, flexible polymers such as polyurethane, nylon, epoxy, etc., and flexible polymer composites such as polyurethane, nylon, epoxy, etc. reinforced with continuous or discontinuous fibers, particles or hollow beads made from metals, polymers, ceramics, glass or minerals, to fill in between or over gap 115 between the overlap plate edges.

Thermal shield 108 may be disposed between carrier mount 106 and test specimen mount 110 such that it insulates strain gage 104 from heat at or near surface 105a of test specimen 105 during use. As depicted, in one embodiment, thermal shield 108 includes a planner rectangular plate of material. Thermal shield 108 may have an area that is greater than an area of carrier mount 106 and/or strain gage 104. For example, edges of thermal shield 108 may extend outward such that heat moving from a surface of the test specimen is directed away from and/or around carrier mount 106 and/or strain gage 104.

In one embodiment, thermal shield 108 includes multiple portions, such as a split plate having a first portion 108a and a second portion 108b. In the illustrated embodiment, first portion 108a and second portion 108b are not directly coupled to one another. In one embodiment, at least a portion of first portion 108a and second portion 108b of thermal shield 108 are disposed proximate one another during use. When portions 108a and 108b are separated split 124 provide a gap 126 between the two portions. Gap 126 may be defined by edges 128 including a first edge surface 128a of first portion 108a and second edge surface 128b of second portion 108b. Edges 128a and 128b may be disposed close enough to one another to inhibit the transfer of heat from at or near surface 105a of test specimen 105 toward stain gage 104 during use. For example, gap 126 may be about 0.25 mm, 0.5 mm, 1 mm, 2 mm, 3 mm, 4 mm, 5 mm, 6 mm, 7 mm, 8 mm, 9 mm, 10 mm, or more during use.

In one embodiment, an interface between edges 128a and 128b may be provided to further inhibit the transfer of heat from the test specimen toward stain gage 104 during use. For example, as depicted, one embodiment may include an overlap 130 of at least a portion of first edge 128a and second edge 128b. In the illustrated embodiment, overlap 130 includes an "S-shaped" overlap. S-shaped overlap 130 includes complementary protrusions 130a and 130b of portions 108a and 108b, respectively, that overlap one another such that gap 126 has a S-shaped path. Overlap 130 and resulting gap 126 may include a path that blocks a straight-line path from a first (bottom) side 132a of thermal shield 108 facing test specimen 105 during use, to a second (top) side 132b of thermal shield 108 opposite the bottom side and facing away from test specimen 105 during use. Protrusions 130a and 130b may be of sufficient length such that as portions 108a and 108b move relative to one another during use, overlap 130 still exists, thereby helping to inhibit the transfer/movement of heat across thermal shield 108 during use.

Other embodiment may include a various types of interfaces between first and second portions 108a and 108b of thermal shield 108. For example, overlap 130 may include shapes such as those described above with respect to FIGS. 3A-3F.

In one embodiment, gap 126 may be spanned by one or more members and materials that provide an elastic, non-rigid, coupling of portions 108a and 108b. For example, gap 126 may employ a flexible insulating material such as but not limited to polymeric and metalized insulated tape, flexible insulating open and closed cell foams, insulating blankets comprised of stitched and/or woven continuous or discontinuous fibers such as polymers, glass, ceramic, mineral, graphite or carbon, flexible polymers such as polyurethane, nylon, epoxy, etc., and flexible polymer composites such as polyurethane, nylon, epoxy, etc. reinforced with continuous or discontinuous fibers, particles or hollow beads made from metals, polymers, ceramics, glass or minerals, to fill in between or over gap 126 between the overlap plate edges.

Specimen mount 110 may include a portion of strain gage mount 102 that is coupled to surface 105a of test specimen 105 during use. In one embodiment, specimen mount 110 includes a first portion 110a coupled to a first location on surface 105a, and a second portion 110b coupled to a second location on surface 105a during use. The first and second locations may include areas on surface 105a of test specimen 105 having strain measured there between. In other words, strain gage mounting system 100 may be used to measure the linear displacement between the first and second locations.

In one embodiment, first portion 110a and second portion 110b each include mounting members 140a and 140b, respectively. In the illustrated embodiment, mounting members 140a and 140b include rectangular shaped plates having a first (bottom) surfaces 141a and 141b that faces test specimen 105 during use and a second (top) surface opposite bottom surfaces 142a and 142b and facing away from test specimen 105 during use. Mounting members 140a and 140b may be directly coupled to surface 105a of test specimen 105 during use. For example, bottom surfaces 141a and 141b of mounting members 140a and 140b may be coupled to surface 105a via one or more techniques including but not limited to mechanical fasteners such as machine screws, nuts and bolts, dowels, clips, clasps, clamps and crimping, metal or plastic weld joints, bonding agents such as organic and inorganic adhesives, and/or permanent and electromagnetic magnets. In some embodiments, mounting members 140a and 140b may include additional features conducive to coupling them to surface 105a. For example, in the illustrated embodiment, mounting members 140a and 140b include spot welding pockets 144a and 144b, respectively. In the illustrated embodiment, spot welding pockets 144a and 144b include holes/slots that extend through mounting members 140a and 140b to facilitate coupling test specimen mount 110 to test specimen 105.

In one embodiment, thermal shield 108 is offset from surface 105a of test specimen 105 during use via specimen mount 110. For example, in the illustrated embodiment, an air gap 150 is provided between a bottom surface 132a of thermal shield 108 and surface 105a of test specimen 105b coupled to bottom surfaces 141a and 141b during use. Air gap 150 may provide additional insulating properties that help to inhibit the transfer of heat from at or near surface 105a to strain gage 104 during use. For example, in one embodiment, passive or actively induced air flow through air gap 150 may help to direct heat away from strain gage 104, thereby helping to insulate it.

In one embodiment, air gap 150 may include an air gaps/path provided between portions of test specimen mount 110 and thermal shield 108. For example, in the illustrated embodiment, air gap 150 includes air gaps 150a and 150b between top surfaces 142a and 142b of mounting plates 140a and 140b and bottom surface 132a of thermal shield 108. Air gaps 150a and 150b may provide additional air paths that provide additional insulating properties that help to inhibit the transfer of heat from at or near surface 105a to strain gage 104 during use.

In one embodiment, air gaps 150a and 150b are provided via standoffs 152 that extend between mounting plates 140 and thermal shield 108. For example, in the illustrated embodiment, standoffs 152 extend between top surfaces 142a and 142b of mounting plates 140a and 140b, and bottom surfaces 132a of first and second portions 108a and 108b of thermal shield 108. In the illustrated embodiment, standoffs 152 include integrated standoffs that are formed integrally with mounting plates 140a and 140b. For example, each portion 110a and 110b includes a mounting plate 140a or 140b and standoffs 152 formed as a single piece. In one embodiment, standoffs 152 may be provided as separate components. For example, standoffs, 152 may be provided as post or spacers provided between thermal shield 108 and mounting plates 140. Standoffs 152 may be made from materials of similar composition to the test specimen material including but not limited to metals, ceramics, glasses, plastics, and metal, ceramic, glass and polymeric matrix composites reinforced with continuous or discontinuous fibers, particles or hollow beads made from metals, polymers, ceramics, glass or minerals.

In the illustrated embodiment, portions 110a and 110b of specimen mount 110 are coupled to thermal shield 108 via specimen mount fasteners 158. As discussed in more detail below, specimen mount fasteners 158 may include a variety of fastening devices, such as threaded-type fasteners, dowel-type fasteners, magnetic-type fasteners, and the like. In the illustrated embodiment, specimen mount fasteners 158 extend through thermal shield portions into standoffs 152, thereby securing specimen mount 110 to an underside of thermal shield 108. In one embodiment, a specimen mount fastener 158 is provided at each standoff 152 of specimen mount 110. For example, in the illustrated embodiment, six specimen mount fasteners 158 may be provided at six standoffs 152. (See FIG. 1B).

In one embodiment, portions of carrier mount 106 are offset from thermal shield 108 during use. For example, in the illustrated embodiment, an air gap 160 is provided between a bottom surface 118a of carrier mount split plate 116 and top surface 132b of thermal shield 108 during use. Air gap 160 may provide additional insulating properties that help to inhibit the transfer of heat from at or near surface 105a to strain gage 104 during use. For example, in one embodiment, passive or actively induced air flow through air gap 160 may help to direct heat away from strain gage 104, thereby helping to insulate it.

In one embodiment, air gap 160 is provided via standoffs 162 that extend between split plate 116 and thermal shield 108. For example, in the illustrated embodiment, standoffs 162 extend between top surfaces 132a of thermal shield 108, and bottom surfaces 118a and 118b of first and second plate portions 116a and 116b of carrier mount 106. In the illustrated embodiment, standoffs 162 include integrated standoffs that are formed integrally with carrier split plates 116a and 116b. For example, each portion 116a and 116b includes carrier plate 116a and 116b and standoffs 162, respectively, formed as a single piece. In one embodiment, standoffs 162 may be made of metals or metal alloys, ceramics, glass, minerals, polymer, ceramic, glass or mineral foams, plastics or metal, ceramic, glass, mineral or polymeric matrix composites, or any combination or layering of these materials. In one embodiment, the composite materials are reinforced with but not limited to continuous or discontinuous fibers, particles or hollow beads made from metals, polymers, ceramics, glass or minerals.

In the illustrated embodiment, portions 116a and 116b of carrier mount 116 are coupled to thermal shield 108 via carrier mount fasteners 168. As discussed in more detail below, carrier mount fasteners 168 may include a variety of fastening devices, such as threaded-type fasteners, dowel-type fasteners, magnetic-type fasteners, and the like. In the illustrated embodiment, carrier mount fasteners 168 extend through thermal shield portion 108a and 108b into standoffs 162, thereby securing carrier specimen mount 106 to an upper side of thermal shield 108. In one embodiment, a carrier mount fastener 168 is provided at each standoff 162 of carrier mount 106. In the illustrated embodiment, four specimen mount fasteners 168 are provided at four of six standoffs 152. (See FIG. 1D).

Figure 4A:
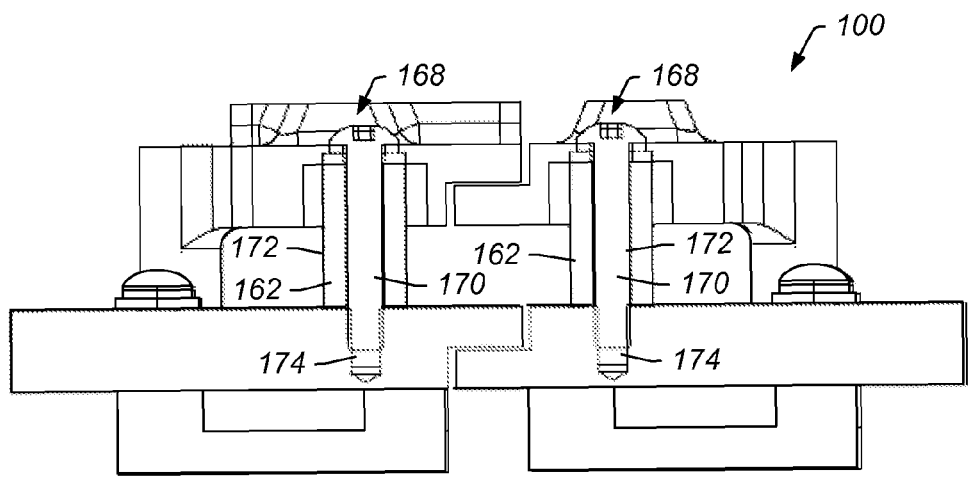
FIGS. 4A-4C are cross-sectional views that illustrate fasteners in accordance with one or more embodiments of the present technique.

Carrier mount fastener 168 may include a variety of fastener types and combinations of fasteners types. In one embodiment, carrier mount fastener 168 includes a threaded fastener. FIG. 4A provides a cross-sectional view of strain gage mounting system 100 that illustrates two carrier mount fasteners 168 in accordance with one or more embodiments of the present technique. In the illustrated embodiment, each carrier mount fastener 168 includes a threaded bolt 170. Bolt 170 is disposed in a through-hole 172 that extends through a standoff 162 of carrier mount 106 and into a complementary threaded hole 174 in thermal shield 108. A similar technique may be used to fasten specimen mount 110 to thermal shield 108.

Figure 4B:
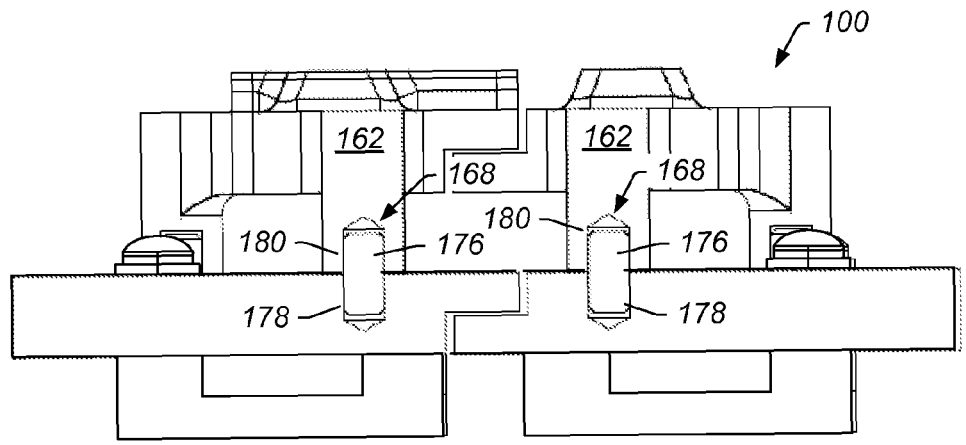

In one embodiment, carrier mount fastener 168 includes a dowel type fastener. FIG. 4B provides a cross-section view of strain gage mounting system 100 that illustrates two dowel-type carrier mount fasteners 168 in accordance with one or more embodiments of the present technique. In the illustrated embodiment, each carrier mount fastener 168 includes a dowel pin 176. One end of dowel pin 176 is disposed in a hole 178 that extends into thermal shield 108 and the other end of dowel pin 176 is disposed in a complementary hole 180 that extends into standoff 162. In one embodiment, dowel pin 176 is secured to holes 178 and 178 via an interference fit, an adhesive, threading or the like. A similar technique may be used to fasten specimen mount 110 to thermal shield 108.

Figure 4C:
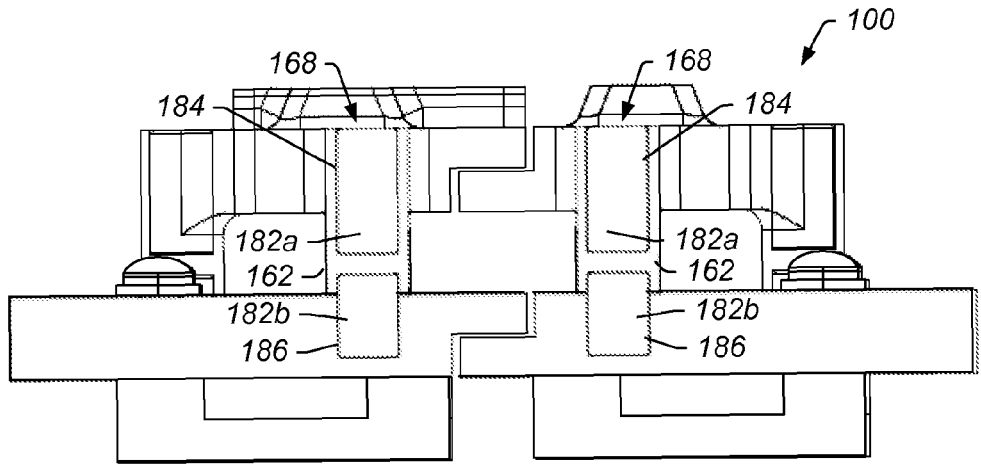

In one embodiment, carrier mount fastener 168 includes a magnetic type fastener. FIG. 4C provides a cross-section view of strain gage mounting system 100 that illustrates two magnetic type carrier mount fasteners 168 in accordance with one or more embodiments of the present technique. In the illustrated embodiment, each carrier mount fastener 168 includes a first portion 182a and a second portion 182b that are magnetically attracted to one another. First portion 182a is disposed in a bore 184 in standoff 162 and second portion 182b is disposed in a bore 186 extending into thermal shield 108. First and second portions 182a and 182b are separated by one another via material at a bottom end of standoff 162. The attraction of magnetic portions 182a and 182b couples carrier mount 106 to thermal shield 108. In one embodiment, bottom ends of standoff 162 may be disposed in a complementary recess in top surface 132b of thermal shield 108, such that lateral force/movement along thermal shield 108 is directly transferred to carrier mount 106. In one embodiment, first portion 182a and 182b may include electro-magnetic devices that provide an attractive force when activated. A similar technique may be used to fasten specimen mount 110 to thermal shield 108.

Additional features may be provided to enhance the ability to inhibit heat from impacting strain gage 104 and or to provide cooling of strain gage 104. In one embodiment, passive thermal cooling devices may be provided. For example, thermal shield 108, carrier mount 106 and/or specimen mount 110 may include fins, cutouts and holes, solid, liquid or gas phase change materials and devices, or heat pipes, that are intended to passively transfer heat from the gage mount thereby reducing the temperature of the attached strain gage 104. In one embodiment, active thermal cooling devices may be provided. For example, thermal shield 108, carrier mount 106 and/or specimen mount 110 may include electric, pneumatic, hydraulic or mechanical fans and blowers, or closed loop fluid cooling systems comprised of pumps, compressors, condensers, evaporators, expansion valves and associated tubing, that are intended to actively transfer heat from the gage mount thereby reducing the temperature of the attached strain gage. In one embodiment, motive and/or electrical power may be provided to active cooling devices via a power generation device locate integral with, on or near strain gage mount 102. For example, thermal shield 108 and/or carrier mount 106 may include devices such as but not limited to solar cell panels, peltier thermoelectric generators or wind turbines, to provide electrical power to the active cooling devices.

Figure 5:
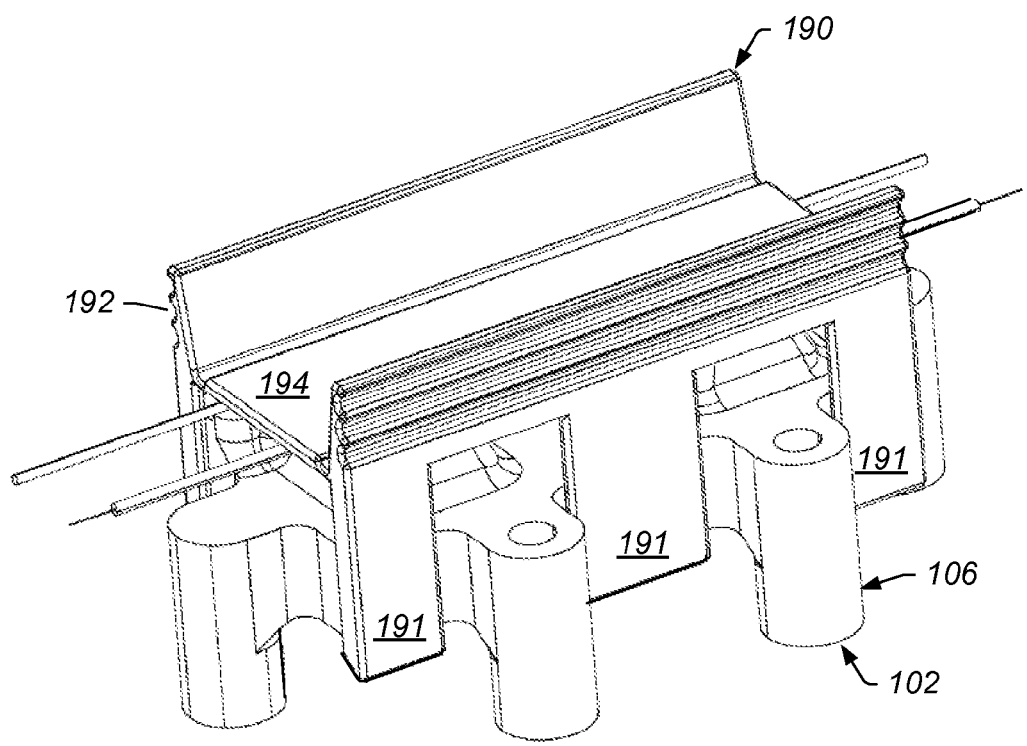
FIG. 5 is a diagram that illustrates an installation tool in accordance with one or more embodiments of the present technique.

In one embodiment, a tool may be used that facilitates installation/mounting of system 100. For example, in one embodiment, a jig or similar alignment device is used to align and retain portions 102*a* and 102*b* such that they can be mounted in a suitable orientation relative to one another. FIG. 5 is an illustration that depicts a tool 190 coupled to strain gage mount 102. In one embodiment, tool 190 includes fingers 191 that couple to strain gage mount 102 to aid in positioning first portion 102*a* and second portion 102*a* during installation. In the illustrated embodiment, sides 192 of tool 102 may be pivoted about a center portion 194 such that fingers 191 are clipped onto carrier mount 106. For example a user may squeeze the upper portions of sides 192 to expand and clip fingers 191 about carrier mount 106 or another portion of system 100. Tool 190 may hold the strain gage mount 102 in position while it is being attached (e.g., welded) onto surface 105*a*. In one embodiment, tool 190 may be formed of an insulating material such that it may insulate a user from electrical currents typically associated with welding. In one such embodiment, a user may grasp tool 190 during installation (e.g., welding) to position system 100 and/or for support during installation. In one embodiment, tool 190 is disposed above strain gage 104. In such an embodiment tool 170 may help to protect strain gage during or after installation.

System 100 may be coupled to various types of test specimen having any variety of surface shapes and textures. For instance, system 100 may be coupled to a curved surface, such as an external wall of a pipe, cylindrical tank, spherical tank or the like. The above described embodiments may be used for coupling to flat or curved surfaces. For example, where surface 105*a* includes a large radius of curvature, surface 105*a* may be substantially flat at the location of mounting system 100. In such an embodiment, bottom surface 111 of mount 110 may be shaped complementary to the shape of surface 105*a*. For example, where surface 105*a* includes a large radius of curvature, surface 105*a* may be substantially flat or slightly curved at the location of mounting system 100, and bottom surface 111 of mount 110 that interfaces with surface 105*a* may be flat or substantially flat. In some embodiments, where surface 105*a* includes a smaller radius of curvature, surface 105*a* may not be substantially flat at the location of mounting system 100. For example, where surface 105*a* includes a small radius of curvature, surface 105*a* may be curved at the location of mounting system 100, and bottom surface 111 of mount 110 that interfaces with surface 105*a* may be curved complementary to the curvature of surface 105*a*. In some embodiments, a shape of surface 111 of mount 110 may be fixed. For example, mount 110 may include a rigid member having a flat or curved bottom surface 111 that couples to surface 105*a*. In some embodiments, a shape of mount 110 may be variable/adjustable. For example, bottom surface 111 may be moved/adjusted between various angles or shapes to be complementary to surface 105*a*. For example, bottom surface 111 of mount 110 may include a flat or curved plate that can be pivoted (e.g., via an adjustment screw) at a variety of angle to be substantially similar in shape to that of surface 105*a*.

Figure 6A:
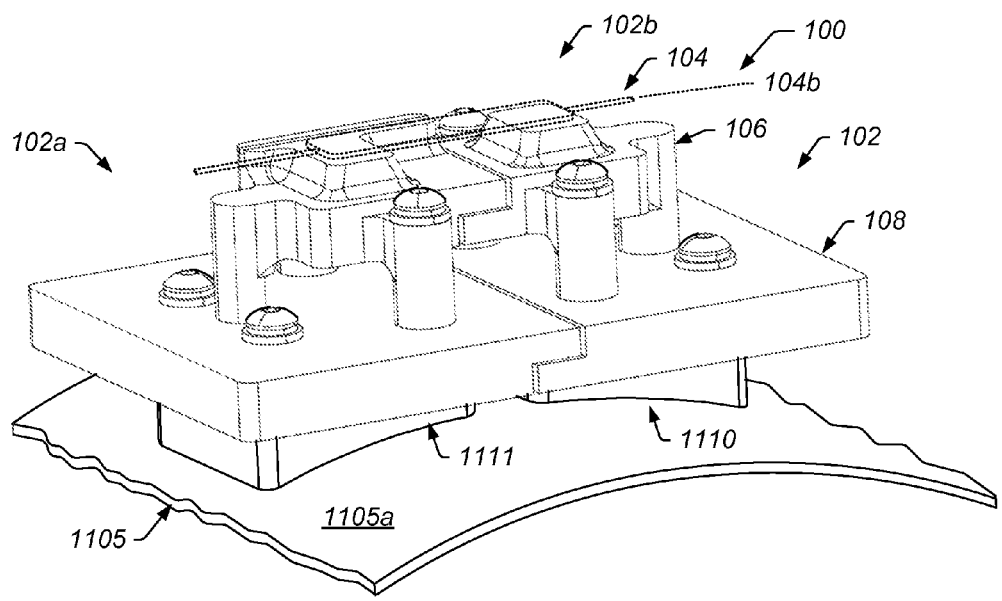
FIGS. 6A and 6B are diagrams that illustrate strain gage mount systems disposed on curved surfaces in accordance with one or more embodiments of the present technique.
Figure 6B:
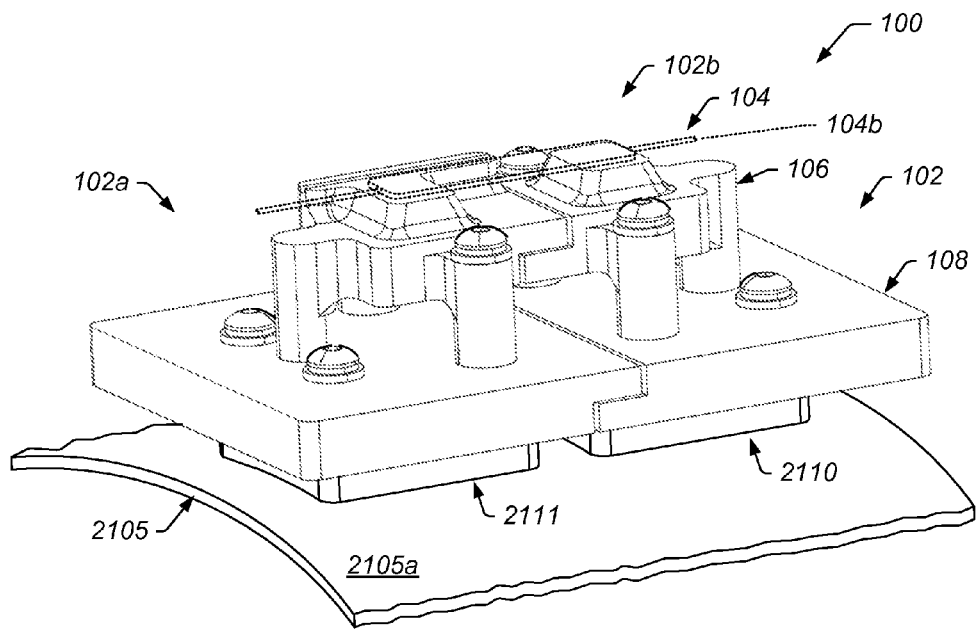

FIGS. 6A and 6B are diagrams that illustrate strain gage mount system 100 disposed on curved surfaces in accordance with one or more embodiments of the present technique. FIG. 6A illustrates system 100 disposed on a curved surface 1105*a* of a test specimen 1105 in accordance with one or more embodiments of the present technique. In the illustrated embodiment, curved surface 1105*a* may include a curvature about a longitudinal axis of test specimen 1105 and/or surface 1105*a* that are substantially perpendicular to the longitudinal axis of fiber optic element 104*b* of strain gage 104. In the illustrated embodiment, system 100 may include a test specimen mount 1110 having a curved bottom surface 1111 that is complementary to the curvature of surface 1105*a*. Test specimen 1105 may be similar to that of test specimen 105 described herein, curved surface 1105*a* may be similar to that of surface 105 described herein, mount 1110 may be similar to that of test specimen mount 110 and bottom surface 1111 may be similar to that of bottom surface 111. described herein. System 100 may be used to detect and measure lateral strain due to circumferential expansion of curved surface 1105*a* in a direction substantially perpendicular to the longitudinal axis of surface 1105*a*. For example, system 100 may detect and measure strain exhibited by an increase in a diameter of curved surface 1105*a* as an internal pressure/temperature of test specimen 1105 increases.

FIG. 6B illustrates system 100 disposed on a curved surface 2105*a* of a test specimen 2105 with one or more embodiments of the present technique. In the illustrated embodiment, curved surface 2105*a* may include a curvature about a longitudinal axis of test specimen 1105 and/or surface 1105*a* that are substantially parallel to the longitudinal axis of fiber optic element 104*b* of strain gage 104. In the illustrated embodiment, system 100 may include a test specimen mount 2110 having a curved bottom surface 2111 that is complementary to the curvature of surface 2105*a*. Test specimen 2105 may be similar to that of test specimen 105 described herein, curved surface 2105*a* may be similar to that of surface 105 described herein, mount 2110 may be similar to that of test specimen mount 110 and bottom surface 2111 may be similar to that of bottom surface 111 described herein. System 100 may be used to detect and measure longitudinal strain due to lengthwise expansion of curved surface 1105*a* in a direction substantially parallel to the longitudinal axis of test specimen 1105 and/or surface 1105*a*. For example, system 100 may detect and measure strain exhibited by an increase in a length of curved surface 1105*a* as an internal pressure/temperature of test specimen 1105 increases.

Other embodiments may include mounting of system 100 on a variety of curved surfaces in a variety of positions. For example, system 100 may be coupled to a curved surface (e.g., via a mount having a complementary curvature to that of the curved surface of the specimen) at any angle oblique to a longitudinal axis of the curved surface (e.g., such that a longitudinal axis of optic element 104 is positioned at about five, ten, fifteen, twenty, twenty-five, thirty, thirty-five, forty, forty-five degrees relative to the a longitudinal axis of the curved surface).

In some embodiments, a test specimen surface may be curved in multiple dimensions. For example, curved surface 1105*a* or 1105*b* may include a sphere or dome shape curved in both lateral and longitudinal directions and mounts 1110 or 2110 may include a bottom surface having a shape/curvature that is complementary to the sphere or dome shapes of curved surfaces 1105*a* or 1105*b*. In such an embodiment, system 100 may be used to detect and measure strain due to lengthwise expansion due to expansion of curved surface 1105*a* or 2105*a*.

Although certain embodiments have been discussed in detail, other embodiments of the system 10 are within the scope of this disclosure. For example, strain gage mounting system 100 mount and attached strain gage are attached to a load cell responsive to the force to be measured, attached to a diaphragm that is responsive to the pressure to be measured, and/or attached to a mass which is responsive to the acceleration to be measured. Embodiments of strain gage mounting system 100 described herein may be used as a high temperature thermally insulated displacement transducer mount.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Furthermore, note that the word "may" is used throughout this application in a permissive sense (i.e., having the potential to, being able to), not a mandatory sense (i.e., must). The term "include", and derivations thereof, mean "including, but not limited to". As used in this specification, the singular forms "a", "an" and "the" include plural referents unless the content clearly indicates otherwise. Thus, for example, reference to "a fastener" includes a combination of two or more fasteners. The term "coupled" means "directly or indirectly connected".

What is claimed is:

1. A strain gage mounting system, comprising:
    a thermal shield, comprising:
        a first thermal shield comprising a first surface configured to face away from a test specimen during use and a second surface configured to face the test specimen during use; and
        a second thermal shield comprising a first surface configured to face away from a test specimen during use and a second surface configured to face the test specimen during use;
        wherein the first thermal shield and the second thermal shield are not rigidly coupled to one another, and wherein at least a portion of the first thermal shield and at least a portion of the second thermal shield overlap one another;
    a strain gage carrier mount disposed on a first side of the thermal shield such that the thermal shield is disposed between the strain gage carrier mount and the test specimen during use, the strain gage carrier mount comprising:
        a first carrier mount rigidly coupled to the first side of the first thermal shield and configured to couple to a first portion of a strain gage carrier; and
        a second carrier mount rigidly coupled to the first side of the second thermal shield and configured to couple to a second portion of a strain gage carrier,
        wherein the first carrier mount and the second carrier mount are not rigidly coupled to one another; and
    a specimen mount disposed on a second side of the thermal shield opposite from the first side of the thermal shield such that the specimen mount is disposed between the thermal shield and the test specimen during use, the specimen mount comprising:
        a first specimen mount rigidly coupled to the second side of the first thermal shield and configured to be coupled to a surface of a test specimen; and
        a second specimen mount rigidly coupled to the second side of the second thermal shield and configured to be coupled to a surface of the test specimen,
        wherein the first specimen mount and the second specimen mount are not rigidly coupled to one another.

2. The strain gage mounting system of claim 1, wherein the first thermal shield and the second thermal shield are configured to be separated from one another via an air gap.

3. The strain gage mounting system of claim 1, comprising a flexible insulating material disposed between the first thermal shield and the second thermal shield.

4. The strain gage mounting system of claim 1, wherein the first carrier mount and the second carrier mount are configured to be separated from one another via an air gap.

5. The strain gage mounting system of claim 1, comprising a flexible insulating material disposed between the first carrier mount and the second carrier mount.

6. The strain gage mounting system of claim 1, wherein at least a portion of the overlap comprises a path between the first thermal shield and the second thermal portion that inhibits air from traveling in a straight-line path between the first side and second side of the thermal shield.

7. The strain gage mounting system of claim 1, wherein at least a portion of the first mount portion and the second carrier mount overlap one another.

8. The strain gage mounting system of claim 1, comprising an air gap between the specimen mount and the thermal shield.

9. The strain gage mounting system of claim 1, comprising one or more standoffs coupled between the first specimen mount and the first thermal shield, and one or more standoffs coupled between the second specimen mount and the second thermal shield.

10. The strain gage mounting system of claim 1, comprising an air gap between the thermal shield and the strain gage carrier mount.

11. The strain gage mounting system of claim 1, comprising one or more standoffs coupled between the first carrier mount and the first thermal shield, and one or more standoffs coupled between the second carrier mount and the second thermal shield.

12. The strain gage mounting system of claim 1, comprising a second thermal shield disposed between the strain gage carrier mount and the test specimen mount.

13. The strain gage mounting system of claim 12, comprising an air gap between the thermal shield and the second thermal shield.

14. The strain gage mounting system of claim 1, comprising a fiber optic strain gage carrier having a first portion coupled to the first carrier and a second portion coupled to the second carrier.

15. The strain gage mounting system of claim 1, comprising an active thermal cooling device configured to inhibit heat transfer between the test specimen and a strain gage coupled to the strain gage carrier mount during use.

16. The strain gage mounting system of claim 15, comprising an electric power generation device configured to provide electrical power to the active thermal cooling device.

17. A strain gage system, comprising:
    a first mounting portion, comprising:
        a first strain gage carrier mount configured to couple to a first end of a strain gage carrier;

a first specimen mount configured to couple to a surface of a test specimen; and
a first thermal shield configured to be disposed between the surface of the test specimen and the first strain gage carrier mount; and
a second mounting portion, comprising:
a second strain gage carrier mount configured to couple to a second end of a strain gage carrier;
a second specimen mount configured to couple to a surface of the test specimen; and
a second thermal shield configured to be disposed between the surface of the test specimen and the second strain gage carrier mount;
wherein at least a portion of an edge of the first thermal shield and at least a portion of an edge of the second thermal shield are configured to be disposed proximate one another during use, and wherein at least a portion of the edge of the first thermal shield and at least a portion of the edge of the second thermal shield overlap one another during use.

18. The strain gage system of claim 17, wherein the first strain gage carrier mount, the first specimen mount, and the first thermal shield are rigidly coupled to one another.

19. The strain gage system of claim 17, wherein the first thermal shield is configured to inhibit the transfer of heat proximate the surface of the test specimen toward a strain gage disposed in the strain gage carrier during use.

20. The strain gage system of claim 17, wherein the first mounting portion and the second mounting portion are not directly rigidly coupled to one another.

21. A strain gage system, comprising:
a substantially planar thermal shielding plate having a first portion and a second portion that are separate from one another, wherein each of the first portion and the second portion comprise a first surface configured to face a test specimen during use and a second surface opposite the first surface configured to face away from the test specimen during use, wherein the first portion and the second portion are disposed adjacent one another during use, and wherein each of the first portion and the second portion comprise an edge that overlap one another during use;
a first mount coupled to the first surface of the first portion of the thermal shielding plate via a standoff, wherein an air gap is provided between the first mount and the thermal shielding plate;
a second mount coupled to the first surface of the second portion of the thermal shielding plate via a standoff, wherein an air gap is provided between the second mount and the thermal shielding plate;
a first strain gage carrier mount coupled to the second surface of the first portion of the thermal shielding plate via a standoff, wherein an air gap is provided between the first strain gage carrier mount and the thermal shielding plate, and wherein the first strain gage mount is configured to couple to a first portion of a strain gage carrier; and
a second strain gage carrier mount coupled to the second surface of the second portion of the thermal shielding plate via a standoff, wherein an air gap is provided between the second strain gage carrier mount and the thermal shielding plate, and wherein the first strain gage mount is configured to couple to a second portion of a strain gage carrier,
wherein the first portion of the thermal shield plate, the first strain gage carrier mount, and the second strain gage carrier mount are configured to move independent of the second portion of the thermal shield plate, the second strain gage carrier mount, and the second strain gage carrier mount.

22. A strain gage mounting system, comprising:
a thermal shield, comprising:
a first thermal shield comprising a first surface configured to face away from a test specimen during use and a second surface configured to face the test specimen during use; and
a second thermal shield comprising a first surface configured to face away from a test specimen during use and a second surface configured to face the test specimen during use;
wherein the first thermal shield and the second thermal shield are not rigidly coupled to one another;
a strain gage carrier mount disposed on a first side of the thermal shield such that the thermal shield is disposed between the strain gage carrier mount and the test specimen during use, the strain gage carrier mount comprising:
a first carrier mount rigidly coupled to the first side of the first thermal shield and configured to couple to a first portion of a strain gage carrier; and
a second carrier mount rigidly coupled to the first side of the second thermal shield and configured to couple to a second portion of a strain gage carrier,
wherein the first carrier mount and the second carrier mount are not rigidly coupled to one another, and wherein at least a portion of the first mount portion and the second carrier mount overlap one another; and
a specimen mount disposed on a second side of the thermal shield opposite from the first side of the thermal shield such that the specimen mount is disposed between the thermal shield and the test specimen during use, the specimen mount comprising:
a first specimen mount rigidly coupled to the second side of the first thermal shield and configured to be coupled to a surface of a test specimen; and
a second specimen mount rigidly coupled to the second side of the second thermal shield and configured to be coupled to a surface of the test specimen,
wherein the first specimen mount and the second specimen mount are not rigidly coupled to one another.

23. A strain gage mounting system, comprising:
a thermal shield, comprising:
a first thermal shield comprising a first surface configured to face away from a test specimen during use and a second surface configured to face the test specimen during use; and
a second thermal shield comprising a first surface configured to face away from a test specimen during use and a second surface configured to face the test specimen during use;
wherein the first thermal shield and the second thermal shield are not rigidly coupled to one another;
a strain gage carrier mount disposed on a first side of the thermal shield such that the thermal shield is disposed between the strain gage carrier mount and the test specimen during use, the strain gage carrier mount comprising:
a first carrier mount rigidly coupled to the first side of the first thermal shield and configured to couple to a first portion of a strain gage carrier; and
a second carrier mount rigidly coupled to the first side of the second thermal shield and configured to couple to a second portion of a strain gage carrier, wherein the first carrier mount and the second carrier mount are not rigidly coupled to one another;

a specimen mount disposed on a second side of the thermal shield opposite from the first side of the thermal shield such that the specimen mount is disposed between the thermal shield and the test specimen during use, the specimen mount comprising
- a first specimen mount rigidly coupled to the second side of the first thermal shield and configured to be coupled to a surface of a test specimen; and
- a second specimen mount rigidly coupled to the second side of the second thermal shield and configured to be coupled to a surface of the test specimen, wherein the first specimen mount and the second specimen mount are not rigidly coupled to one another; and an active thermal cooling device configured to inhibit heat transfer between the test specimen and a strain gage coupled to the strain gage carrier mount during use.

24. The strain gage mounting system of claim 23, further comprising an electric power generation device configured to provide electrical power to the active thermal cooling device.

* * * * *